US008790928B2

(12) United States Patent
Gorr

(10) Patent No.: US 8,790,928 B2
(45) Date of Patent: Jul. 29, 2014

(54) UTILISATION OF CONSTRUCTS COMPRISING RECOMBINATION SEQUENCE MOTIFS FOR ENHANCING GENE EXPRESSION IN MOSS

(75) Inventor: Gilbert Gorr, Freiburg (DE)

(73) Assignee: Greenovation Biotech GmbH, Freiburg (DE)

( * ) Notice: Subject to any disclaimer, the term of this patent is extended or adjusted under 35 U.S.C. 154(b) by 1291 days.

(21) Appl. No.: 10/566,496

(22) PCT Filed: Jul. 29, 2004

(86) PCT No.: PCT/EP2004/008521
§ 371 (c)(1),
(2), (4) Date: Jan. 31, 2006

(87) PCT Pub. No.: WO2005/014830
PCT Pub. Date: Feb. 17, 2005

(65) Prior Publication Data
US 2008/0248523 A1    Oct. 9, 2008

(30) Foreign Application Priority Data
Jul. 31, 2003  (EP) .................... 03017343

(51) Int. Cl.
*C12N 15/82* (2006.01)
*C12N 15/00* (2006.01)
*C12N 15/09* (2006.01)

(52) U.S. Cl.
USPC .................. 435/468; 435/69.1; 435/320.1

(58) Field of Classification Search
None
See application file for complete search history.

(56) References Cited

U.S. PATENT DOCUMENTS

| 4,684,611 A | 8/1987 | Schliperoort et al. |
| 5,100,792 A | 3/1992 | Sanford et al. |
| 6,391,642 B1 * | 5/2002 | Resnick et al. ............... 435/483 |
| 2003/0113921 A1 * | 6/2003 | Gilbertson et al. ........... 435/475 |
| 2006/0035269 A1 * | 2/2006 | Hartley et al. .................... 435/6 |

FOREIGN PATENT DOCUMENTS

| DE | 40 05 152 A1 | 8/1991 |
| EP | 0 175 966 A1 | 4/1986 |
| EP | 0 290 395 A2 | 5/1988 |
| EP | 0 331 083 A2 | 2/1989 |
| EP | 0 434 616 A1 | 12/1990 |
| EP | 0 444 882 B1 | 2/1991 |
| EP | 1 206 561 B1 | 9/2000 |
| WO | WO 87/06614 | 11/1987 |
| WO | WO 90/12096 | 10/1990 |
| WO | WO 92/09696 | 6/1992 |
| WO | WO 94/00583 | 1/1994 |
| WO | WO 01/12456 A2 | 4/2001 |
| WO | WO 02/097080 A2 | 12/2002 |

OTHER PUBLICATIONS

Schaefer, Annual Review of Plant Physiology and Plant Molecule Biology, 53:477-501, 2002.*
Degryse et al., Yeast 11:629-640, 1995.*
Bubeck et al., Nucl. Acids Research, 21 (15): 3601-3603, 1993.*
Zhang Jun et al. "Expression of thymosin a in *Synechococcus* sp. PCC7942 by homology inegration donor plasmid pUTK" Marine Sciences. vol. 25, No. 6. pp. 1-4, 2001.
Assaad, Epigenetic repeat-induced gene silencing (RIGS) in *Arabidopsis*, Plant Mol. Biol. 22:1067-1085 (1993).
Borisjuk, Production of recombinant proteins in plant root extracts, Nature Biotechnology 17:466-469 (1999).
Caddick, An ethanol inducible gene switch for plants used to manipulate carbon metaboloism, Nature Biotechnology 16:177-180 (1998).
Depicker, Nopaline synthase: transcript mapping and dna sequence, J. Mol. Appl. Genet. 1(6):561-573 (1982).
Engel, The induction of Biochemical and Morphological mutants in the moss *Physcomitrella patens*, Amer. J. Biot. 55(4):438-446 (1968).
Freeman, A comparison of methods for plasid delivery into plant protoplasts, Plant & Cell Physiol. 25(8)1353-1365 (1984).
Gorr, Biotechnologishe nutzung von *Physcomitirella patens*, Dissertation (1999).
Gorr et al, Using a moss for the expression of recombinant human vascular endothelial growth factor: an alternative, Nauyn-Schmiedeberg's Arch. Pharmacol. 329 Suppl.R86 (2001).
Grimsley et al. The production of somatic hybrids by protoplast fusion in the moss, *Physcomitrella patens* Molec. gen. Genet 154:97-100(1977).
Herlitschka et al, Overexpression of human prothrombin in permanent cell lines using a dominant selection/amplification fusion marker, Prot. Express. and Pur 8, 358-364 (1996).
Hohe et al., Optimsiation of a bioreactor culture of the moss *Physcomitrella patens* for mass production of protoplasts, Plant Sci 165:354-358 (1985).
Kammerer et al., Genetic analysis of the effects of retransformation of transgenic lines of the moss *Physcomitrella patens*, Mol. Gen. Genet. 250:380-382 (1996).
Kindle, High-frequency nuclear transformation of *Chylamydomonas reinhardtii*, Proc. Natl. Acad. Sci. 87:1228-1232 (1990).
Ma et al, Intrinsic direct repeats generate consistent post-transcriptional gene silencing in tobacco, Plant J. (2002) Abstract.
Oard, Physical methods for the trasformation of plant cells, Biotech. Adv. 6:1-11 (1991).
Pearson, Rapid and sensitive sequence comparison with fastp and fasta, Methods in Enymology 183:63-98 (1990).
Reski et al, Genome anaylsis of moss *Physcomitrella patens*, Mol Gen Genet 244:352-359 (1994).
Reski et al, Induction of budding on chloronemata and caulonemata of the moss, *Physcomitrella patents*, using isopentyladenine, Planta 165:354-358 (1985).
Reutter et al, Production of a heterologous protein in bioreactor cultures of fully differentiated moss plants, Plant Tissue Culture and Biotechnology 2(3)142-147, 1996.
Ringold, Co-expression and amplification of dihydrofolate reductase cDNA and the *Escherichia coli* XGPRT gene in chinese hamster ovary cells, J Mol Appl Genet 1(3):165-75 (1985.

(Continued)

*Primary Examiner* — Nancy T Vogel
(74) *Attorney, Agent, or Firm* — Biotech Beach Law Group, PC; Raymond Wagenknecht

(57) ABSTRACT

A method of amplifying gene expression in a moss plant cell or moss tissue, DNA constructs therefor, moss plant cells and uses thereof for the production of protein.

19 Claims, No Drawings

(56) References Cited

OTHER PUBLICATIONS

Rother, Fate of a mutant macrocholoplast in somatic hybrids, J. Plant Physiol. 143:72-77 (1994).

Schaefer, A new moss genetics: targeted mutagenesis in *Physcomitrella patens*, Annu. Rec. Plant. Biol. 53:477-501 (2002).

Schaefer, Stable transformation of the moss *Physcomitrella patens*, Mol. Gen. Genetics 226:418-424 (1991).

Schaefer, Principles and protocols for the moss *Physcomitrella patens*, http://www.unil.ch/lpc/docs/PPprotocols2001.pdf (2001).

Strep et al, Plant nuclear gene knockout reveals a role in plastid division for the homolog of the bacterial cell division protein FtsZ Proc Natl Acad Sci 95:4368-4373 (1998).

Topfer et al. Versatile cloning vectors for transient gene expression and direct gene transfer in plant cells, NAR 16:8725 (1988).

Topfer et al, A set of plant expression vectors for transcriptional and translational fusions, NAR15, 5890 (1987).

Zeidler et al, Transgene expression in the moss *Ceratodon purpeus*, J Plant Physiol. 154:641-550 (1999).

\* cited by examiner

SEQUENCE LISTING

```
<160> NUMBER OF SEQ ID NOS: 12

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Primer
      MoB323

<400> SEQUENCE: 1
atactcgagg aagatgaact tttctgcctg tcttgg                            36

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence:  Primer
      MoB349

<400> SEQUENCE: 2
ctgccatggg tgcagcctgg gaccac                                       26

<210> SEQ ID NO 3
<211> LENGTH: 250
<212> TYPE: DNA
<213> ORGANISM: Physcomitrella patens
<220> FEATURE:
<221> NAME/KEY: intron
<222> LOCATION: (1)..(250)
<223> OTHER INFORMATION: 5' sequence of the 5th intron of the alpha
      1,3-fucosyltransferase gene

<400> SEQUENCE: 3
gcggaaatgt tcagagttaa gcgaaatcac aactaaaaga gattggaagc agaagaattt   60
ttgagcagct gttcttaatt cacgcaacga caacgctatt aactgtatgt gtagacgatg  120
cactttcgta ctgaagggat ctaaatttat tatatcccttt cataactaga ggcaaggcgg  180
aaatcacaaa actattggta cctacgtact acagcctcca ggatcaaaca taagagtgaa  240
acactggacc                                                        250

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Upstream
      primer Rec1_SalI_SacII
```

```
<400> SEQUENCE: 4
gaggtcgacc cgcggaaatg ttcagag                                        27

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Downstream
      primer Rec1_SmaI

<400> SEQUENCE: 5
ctccccgggt ccagtgtttc actc                                           24

<210> SEQ ID NO 6
<211> LENGTH: 208
<212> TYPE: DNA
<213> ORGANISM: Physcomitrella patens
<220> FEATURE:
<221> NAME/KEY: intron
<222> LOCATION: (1)..(208)
<223> OTHER INFORMATION: 3' sequence of the alpha 1,3-fucosyltransferase
      gene

<400> SEQUENCE: 6
gggacccaag cgtaagaagt cttatgaaaa agttacctca cagattaaaa ctaaacatag    60
gaaaatacca atgcactcca atgtgtcaat gagattaacg cttgactaac atgaaaatat  120
aaatattcac cgaatgaaag aaattagaaa acaggacctg tagattgtaa gagatagatt  180
cttgagttag aaacacaaat gattgtcc                                      208

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Upstream
      primer Rec11_SmaI

<400> SEQUENCE: 7
gagcccggga cccaagcgta agaag                                          25

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Downstream
      primer Rec11_SacII_SsTII

<400> SEQUENCE: 8
tctgagctcc cgcggacaat catttgtgtt tc                                  32

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Upstream
      primer Rec2_SalI_SacII

<400> SEQUENCE: 9
gaggtcgacc cgcggaccca agcgtaagaa g                                   31

<210> SEQ ID NO 10
```

```
<211> LENGTH: 26
<212> TYPE: DNA
<213> ORGANISM: Artificial Sequence
<220> FEATURE:
<223> OTHER INFORMATION: Description of Artificial Sequence: Downstream
      primer Rec2_SmaI

<400> SEQUENCE: 10
tctcccggga caatcatttg tgtttc                                          26

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Upstream
      primer Rec22_SmaI

<400> SEQUENCE: 11
gagcccggga aatgttcaga gttaagcg                                        28

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Downstream
      primer Rec22_SacII_SstI

<400> SEQUENCE: 12
tctgagctcc cgcggtccag tgtttcactc ttatg                                35
```

UTILISATION OF CONSTRUCTS COMPRISING RECOMBINATION SEQUENCE MOTIFS FOR ENHANCING GENE EXPRESSION IN MOSS

This is a National Phase Application in the United States of International Patent Application No. PCT/EP2004/008521 filed Jul. 29, 2004, which claims priority on European Patent Application No. 03017343.9, filed Jul. 31, 2003. The entire disclosures of the above patent applications are hereby incorporated by reference.

This application incorporates by reference the Sequence Listing on the compact disc, namely the file "Sequence-listing.APP" created on Jan. 26, 2006 with a size of 4 kilobytes.

BACKGROUND OF THE INVENTION

The present invention relates to methods and materials for improving gene expression in eucaryotic cells, particularly in plant cells comprised in mosses, such as moss protonema cells.

RELATED ART

Gene amplification for improving the expression of recombinant proteins in mammalian cell cultures is a generally used strategy (Herlitschka et al. (1996) *Protein Expr. Purif.* 8, 358-364; Ringold et al. (1981) J. Mol. Appl.).

In plants, effecting gene amplification strategies is problematic due to silencing events that can be triggered by multi-copy integrations of heterologous DNA (Asaad et al. (1993) *Plant Mol. Biol.* 22, 1067-1085). Recently, strategies for gene amplification in plants have been developed to overcome these limitations. The cis-acting genetic element aps was isolated from a non-transcribed spacer region of tobacco ribosomal DNA. This spacer element was fused to reporter genes of interest and resulted in in higher expression levels of heterologous proteins therefrom (Borisjuk et al. (2000) *Nature Biotechnol.* 18, 1303-1306).

A further strategy has been described by Klimyuk et al. which involved the expression of heterologous proteins via trans-splicing (WO 02/097080).

To date, little is known about the correlation of copy number and heterologous gene expression in transgenic moss plants. The use of mosses for the production of recombinant proteins is a well-established technology (EP1206561, Gorr et al. 2001, *Naunyn-Schmiedeberg's Arch. Pharmacol.* 363 Suppl.: R 85). Typically, anything from 1 to about 50 copies of the transforming plasmid may be integrated into the genome of transformed moss tissue (Schaefer (2002) Annu. Rev. Plant Biol. 53, 477-501). Depending on the design of the transforming constructs employed, homologous recombination, that is, a targeted integration event and/or heterologous recombination, that is, a random or non-targeted integration event can occur. Thus, by using DNA sequences (i.e. comprised of coding or non-coding sequences) for transformation which are homologous to genomic DNA sequences of a moss can result in one or more homologous recombination events via integration of the introduced or transforming DNA into the genomic locus of the homologous DNA. Use of DNA sequences (i.e. comprised of coding or non-coding sequences) for transformation that lack any appreciable homology to a genomic DNA sequence of a moss can result in one or more heterologous recombination events via integration of the introduced DNA randomly into the genome. Moss is the only known plant system which displays a high frequency of homologous recombination (Strepp et al. (1998) *Proc. Natl. Acad. Sci. USA* 95, 4368-4373; Schaefer (2002) Annu. Rev. Plant Biol. 53, 477-501). This apparently unique attribute of mosses has been used for the targeted introduction of genes. However, the amplification of gene expression by increasing the copy number of plasmids of interest in order to generate greater levels of protein per unit mass of stably transformed moss tissue has not hitherto been described.

Surprisingly, it has been found that by transforming, typically co-transforming cells (protoplasts) of moss tissue with at least two heterologous nucleic acid sequences comprising at least one set of recombination sequences results in an increase in the integrated copy number of heterologous nucleic acid constructs in regenerated tissue, such as cells comprised in moss protonema, which in turn is correlated with an increase of protein expression levels.

It is therefore an object of the invention to provide an improved method for the production of proteins of interest in cells comprised in moss tissue.

BRIEF SUMMARY OF THE INVENTION

According to the present invention there is provided a method of amplifying gene expression in a moss plant cell comprising
1) providing at least a first heterologous nucleic acid construct comprising at least one heterologous nucleotide sequence operably linked to a promoter, wherein the said construct is flanked at the 5' end thereof by a first recombination sequence and is flanked at the 3' end of the said construct by a second recombination sequence in the same orientation as the first;
2) providing at least a second heterologous nucleic acid construct comprising at least one heterologous nucleotide sequence operably linked to a promoter, wherein the said construct is flanked at the 5' end thereof by said second recombination sequence and is flanked at the 3' end of the said construct by said first recombination sequence in the same orientation as the second; and
3) transforming into the moss plant cell at least said first and said second heterologous nucleic acid construct.

The skilled addressee will appreciate that once the said at least two heterologous constructs are transformed into the moss plant cell, such as a moss protoplast, for example a *Physcomitrella patens* protoplast, which is then permitted to regenerate into moss protonema, for example of *Physcomitrella patens*, they will undergo recombination with each other many times over. This process, once initiated in the moss plant cell, increases the copy number of integrated transforming DNA constructs of the invention therein.

Thus, as a further aspect of the invention there is provided a moss protonema, preferably protonema of *Physcomitrella patens*, comprised of cells stably transformed, more preferably co-transformed with at least two complementary constructs of the invention.

Ultimately, significant increases in the level of heterologous protein of interest from the at least one heterologous gene of interest are measurable over and above the levels of protein that are measurable in moss protonema cells from conventional transforming constructs lacking the features of constructs of the invention. The at least first and the at least second recombination sequences form a complementary set that make it possible for the constructs of the invention to recombine with each other. Naturally, the skilled addressee will appreciate that constructs of the invention may be employed in which one or more complementary sets of recombination sequences may be used depending on how many of the same or different nucleotide sequences of interest are intended to be utilised for protein production, such as 1, 2, 3, 4, or 5 or more sets. Preferably a single complementary set of recombination sequences is used for ease of convenience.

In a further aspect of the invention there is provided a heterologous DNA construct of the invention that comprises in the 5' to 3' direction:

1) an introduced first recombination sequence;
2) at least a heterologous nucleic acid sequence of interest comprising a promoter operably linked thereto and optionally a terminator therefor; and
3) an introduced second recombination sequence.

In a further aspect of the invention there is provided a heterologous DNA construct of the invention that comprises in the 5' to 3' direction:

1) an introduced second recombination sequence;
2) at least a heterologous nucleic acid sequence of interest comprising a promoter operably linked thereto and optionally a terminator therefor; and
3) an introduced first recombination sequence.

Thus the two constructs comprise similar complementary recombination sequences located at different sites therein that enable or permit the constructs to recombine with each other in situ in transformed moss protonema cells comprised in the moss protonema, for example protonema of *Physcomitrella patens*. Preferably, the constructs of the invention are in linear form.

Such constructs may be used to transform moss protoplasts in at least two separate transformation events where a first transformation event is separated from a second transformation event in time or the constructs of the invention may be co-transformed into moss protoplasts which are then permitted or allowed to regenerate into moss protonema. Preferably, the transformation event comprises co-transforming moss protoplasts with at least two constructs of the invention as described above.

The recombination sequence utilised in constructs of the invention may be any sequence selected from any organism, such as from plant genomic DNA, such as from genomic DNA, cDNA, intron or exon regions or non-coding regions or any combination thereof, for example, from *Physcomitrella patens*. Suitable genomic DNA for use as recombination sequence may comprise DNA from an exon or an intron or a hybrid of the two. Preferably the recombination sequence is formed of DNA from an intron or non-coding region of DNA. As discussed herein, the orientation of the two flanking recombination sequences is preferably in the same orientation, for example, in the 5' to 3' direction or in the 3' to 5' direction in both of the two transforming constructs albeit that the actual location of the recombination sequences within the two constructs is different one from the other as alluded to above. Naturally, the skilled addressee will appreciate that the heterologous constructs of the invention will comprise recombination sequences in appropriate position and orientation that enables recombination events to occur between the two. The recombination nucleotide sequences of constructs of the invention can be of any length provided that they are capable of causing or permitting recombination events to occur. Suitable lengths for the recombination sequences employed in constructs of the invention range from 25-1000 nucleotides in length or longer; from 25-650 nucleotides in length; from 50-650 nucleotides in length; from 100-400 nucleotides in length; or from 200-400 nucleotides in length, for example, of about 200+/−50 nucleotides in length. The skilled addressee will appreciate that the length of the recombination sequences of constructs of the invention may vary depending on design.

As a further aspect of the invention, there is provided a moss cell comprised of constructs of the invention, moss protonema comprised of said moss cells, and/or moss plants comprising constructs of the invention, particularly a moss protonema cell, moss protonema comprised of protonema cells comprised of constructs of the invention, and/or moss plants comprised of constructs of the invention that are *Physcomitrella patens*.

Particular aspects of the invention will now be discussed in more detail.

DETAILED DESCRIPTION OF THE INVENTION

Definitions

The term "heterologous" is used broadly below to indicate that the gene/sequence of nucleotides in question have been introduced into moss protoplasts using genetic engineering, i.e. by human intervention. A heterologous gene may augment the expression of a protein of interest from an endogenous equivalent gene, i.e. one which normally performs the same or a similar function, or the inserted sequence may be additional to the endogenous gene or other sequence. Nucleic acid heterologous to a cell may be non-naturally occurring in moss protoplasts of that type, variety or species. Thus the heterologous nucleic acid may comprise a coding sequence of, or derived from, a particular type of organism, such as a mammalian species, e.g of human, ovine, bovine, equine, or porcine species, placed within the context of a moss protoplast, such as a protoplast derived from *Physcomitrella patens*. A further possibility is for a nucleic acid sequence to be placed within a moss protoplast in which it or a homologue is found naturally, but wherein the nucleic acid sequence is linked and/or adjacent to nucleic acid which does not occur naturally within the cell, or cells of that type or species or variety of plant, such as operably linked to one or more regulatory sequences, such as a promoter sequence, for control of expression.

"Gene" unless context demands otherwise refers to any nucleic acid encoding genetic information for translation into a peptide, polypeptide or protein.

"Vector" is defined to include, inter alia, any plasmid, cosmid, phage, or viral vector in double or single stranded linear or circular form which may or may not be self transmissible or mobilizable, and which can transform a prokaryotic or eukaryotic host and exists extrachromosomally (e.g. autonomous replicating plasmid with an origin of replication). Specifically included are shuttle vectors by which is meant a DNA vehicle capable, naturally or by design, of replication in two different host organisms, which may be selected from actinomycetes and related species, bacteria and eucaryotic (e.g. higher plant, mosses, mammalian, yeast or fungal) cells.

"Expression vector" refers to a vector in which a nucleic acid is under the control of, and operably linked to, an appropriate promoter or other regulatory elements for transcription in a host cell such as a microbial cell or a moss protoplast. The vector may be a bi-functional expression vector which functions in multiple hosts. In the case of genomic or subgenomic DNA, this may contain its own promoter or other regulatory elements and in the case of cDNA this may be under the control of an appropriate promoter or other regulatory elements for expression in the host cell.

A "promoter" is a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus.

The invention also embraces use of a variant of any of these sequences. A variant protein shares homology with, or is identical to, all or part of the sequences discussed above. Generally speaking, wherever the term is used herein, variants may be:
(i) naturally occurring homologous variants of the relevant protein,
(ii) artificially generated homologous variants (derivatives) which can be prepared by the skilled person in the light of the present disclosure, for instance by site directed or random mutagenesis, or by direct synthesis. Preferably the variant nucleic acid, encoding the variant polypeptide, is generated either directly or indirectly (e.g. via one or more amplification or replication steps) from an original nucleic acid. Changes to the nucleic acid sequence may produce a derivative by way of one or more of addition, insertion, deletion or substitution of one or more nucleotides in the nucleic acid, leading to the addition, insertion, deletion or substitution of one or more amino acids in the encoded polypeptide. Desirable mutation may be random or site directed mutagenesis in order to alter the activity (e.g. specificity) or stability of the encoded polypeptide. Changes may be by way of conservative variation, i.e. substitution of one hydrophobic residue such as isoleucine, valine, leucine or methionine for another, or the substitution of one polar residue for another, such as arginine for lysine, glutamic for aspartic acid, or glutamine for asparagine. Also included are variants having non-conservative substitutions. In regions which are critical in determining the peptides conformation or activity such changes may confer advantageous properties on the polypeptide e.g. altered stability or specificity.

Similarity or homology in the case of variants is preferably established via sequence comparisons made using FASTA and FASTP (see Pearson & Lipman, 1988. Methods in Enzymology 183: 63-98). Parameters are preferably set, using the default matrix, as follows:
Gapopen (penalty for the first residue in a gap): −12 for proteins/−16 for DNA
Gapext (penalty for additional residues in a gap): −2 for proteins/−4 for DNA
KTUP word length: 2 for proteins/6 for DNA.

Homology may be at the nucleotide sequence and/or encoded amino acid sequence level. Preferably, the nucleic acid and/or amino acid sequence shares at least about 75%, or 80% identity, most preferably at least about 90%, 95%, 96%, 97%, 98% or 99% identity.

Homology may also be assessed by use of a probing methodology (Sambrook et al., 1989). One common formula for calculating the stringency conditions required to achieve hybridization between nucleic acid molecules of a specified sequence homology is: $T_m = 81.5°$ C.$+16.6$ Log [Na+]$+0.41$ (% G+C)$-0.63$ (% formamide)$-600/\#bp$ in duplex. As an illustration of the above formula, using [Na+]=[0.368] and 50-% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

Use in Moss Plants

As described below, in its various aspects, the invention will generally be employed on moss protoplasts, using nucleic acids encoding proteins of interest.

Suitable promoters which operate in moss protoplasts include the Cauliflower Mosaic Virus 35S (CaMV $^{35}$S). Other examples are disclosed at pg 120 of Lindsey & Jones (1989) Plant Biotechnology in Agriculture" Pub. OU Press, Milton Keynes, UK. The promoter may be selected to include one or more sequence motifs or elements conferring developmental and/or tissue-specific regulatory control of expression. Inducible plant promoters include the ethanol induced promoter of Caddick et al (1998) Nature Biotechnology 16: 177-180.

A terminator is contemplated as a DNA sequence at the end of a transcriptional unit which signals termination of transcription. These elements are 3'-non-translated sequences containing polyadenylation signals, which act to cause the addition of polyadenylate sequences to the 3' end of primary transcripts. For expression in plant cells the nopaline synthase transcriptional terminator (A. Depicker et al., 1982, J. of Mol. & Applied Gen. 1:561-573) sequence may serve as a transcriptional termination signal, as can the CaMV 35S terminator (Töpfer et al. (1987) NAR 15, 5890).

If desired, selectable genetic markers may be included in further conventional constructs, such as circular plasmids or in further linearised DNA constructs that are co-transformed into a moss cell of the invention, such as those that confer selectable phenotypes such as resistance to antibiotics or herbicides (e.g. kanamycin, hygromycin, phosphinotricin, chlorsulfuron, methotrexate, gentamycin, spectinomycin, imidazolinones and glyphosate).

The present invention also provides methods comprising the introduction of such constructs comprising appropriate heterologous sequences into a moss plant cell and/or induction of expression of a construct of the invention within a moss plant cell, by application of a suitable stimulus e.g. an effective exogenous inducer. Suitable moss plant cells include the moss protoplast, and cells comprised in the protonema, such as those derived from *Physcomitrella patens*.

Nucleic acid can be introduced into moss protoplasts using any suitable technology, such as PEG-mediated DNA uptake as herein described, particle or microprojectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614 Gelvin Debeyser) other forms of direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d) Physical methods for the transformation of plant cells are reviewed in Oard, 1991, *Biotech. Adv.* 9: 1-11.

Electroporation, PEG-mediated DNA uptake and direct DNA uptake are preferred. Especially preferred is the modified PEG mediated DNA uptake procedure as disclosed in the examples herein.

The particular choice of a transformation technology will be determined by its efficiency to transform certain moss species as well as the experience and preference of the person practising the invention with a particular methodology of choice. It will be apparent to the skilled person that the particular choice of a transformation system to introduce nucleic acid into moss protoplasts is not essential to the invention. However, the use of the PEG-mediated DNA transformation system as described herein is preferred.

Thus various aspects of the present invention provide a method of transforming a moss protoplast involving introduction of a heterologous nucleic acid-based construct of the invention as described herein into a moss protoplast and regeneration of the protoplast into protonema tissue and causing or allowing expression of protein from the constructs of the invention. Thus, the skilled addressee may expect that expression of protein targeted to the cytosol or other cellular compartments can be improved by using constructs and methods of the invention. Preferably, recombinant proteins produced by the methods of the invention are secreted into the medium from stably transformed protonemal tissue.

Thus, by employing the at least two constructs of the invention as herein described production lines may be generated harbouring high copy numbers of the target gene which in turn results in high protein yields over the cultivation period in a suitable bioreactor.

Choice of Genes to Enhance

Genes of interest include those encoding proteins which are themselves, natural medicaments such as pharmaceuticals or veterinary products.

Heterologous nucleic acids may encode, inter alia, genes of bacterial, fungal, plant or animal origin. Polypeptides produced may be utilised for producing polypeptides which can be purified therefrom for use elsewhere. Such proteins include, but are not limited to retinoblastoma protein, p53, angiostatin, and leptin. Likewise, the methods of the invention can be used to produce mammalian regulatory proteins. Other sequences of interest include proteins, hormones, such as follicle stimulating hormone, growth factors, cytokines, serum albumin, haemoglobin, collagen, thaumatin, thaumatin-like proteins, epidermal growth factors such as VEGF, heterodimers, antibodies, immunoglobulins, fusion antibodies and single chain antibodies.

Expression of Target Genes

Generally speaking, heterologous nucleic acids may be expressed by any appropriate process used in the art or they may be transcribed or expressed as follows:
(i) expression of 'naked' DNA e.g. comprising a promoter operably linked to the heterologous sequence in a construct of the invention,
(ii) expression from an expression vector, such as a replicating vector. Generally speaking, those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press or *Current Protocols in Molecular Biology*, Second Edition, Ausubel et al. eds., John Wiley & Sons, 1992.

As discussed above, the present inventors show that enhanced expression from constructs of the invention introduced (preferably at high levels) into the protoplasts of a moss, preferably at high cell density, such as *Physcomitrella patens*, which constructs are integrated into the genome give rise to transcribed mRNA.

Thus in one aspect of the invention there is disclosed use of a transformed moss protoplast capable of generating mRNA encoding a target protein generated by transcription from an introduced nucleic acid construct of the invention including the target nucleotide sequence operably linked to a promoter, which construct is introduced into the cell of an organism.

The "introduced nucleic acid" will thus include the heterologous nucleic acid sequence as a DNA sequence provided in the form of a construct of the invention that is capable of giving rise to the production of extracellular protein at an elevated level relative to the level of protein production normally associated with stable transgene expression of the said DNA sequence. In one aspect of the invention, the heterologous nucleic acid sequence may encode a protein that is made up of a signal and/or a transit peptide coupled to the protein or polypeptide sequence of choice.

The reporter can be any detectable protein, such as a marker gene, commonly used in the art such as GUS, GFP, luciferase etc. Preferably, the reporter is a non-invasive marker such as GFP or luciferase.

Naturally, the man skilled in the art will recognise that more than one heterologous nucleic acid sequence may be used in the, or each, construct of the invention, although a single sequence in each case is preferred. Multiple vectors (each including one or more nucleotide sequences encoding heterologous protein of choice) may be introduced into the moss protoplasts via PEG-mediated DNA uptake methods as described herein. This may be useful for producing e.g. multiple subunits e.g. of an enzyme.

In a further embodiment of the invention high levels of fully and correct assembled proteins consisting of multiple subunits can be achieved by influencing the stoichiometry of the different coding nucleic acid sequences integrated into the genome.

The amount of proper assembled protein that consists of multiple subunits is dependent on the stoichiometry of the subunits on the protein level. In the case of subunits which have to be targeted to different compartments via signal peptides e.g. to the secretory pathway, the stoichiometry is not only influenced by the expression derived from e.g. promoter and transcriptional signals but also by the targeting signal and processing of targeting signal, e.g. proper cleavage of the signal peptide. In this aspect of the invention use of non-equimolar quantities of the nucleic acid sequences coding for the different subunits may be appropriate for multimeric proteins, e.g. for immunoglobulins. Non-equimolar quantities of coding nucleic acids resulting in proper stoichiometry of multiple subunits of a dimeric or multimeric protein can thus be achieved by providing appropriately designed constructs of the invention that enable correct assembly of the different subunits.

As described in the Examples below, expression of heterologous sequences using methods of the invention when introduced in this way can give very high levels of target polypeptide over the course of the expression period, which will generally be several days, depending on the precise methods and materials employed. By using the methods of the invention as herein described, high levels of heterologous polypeptide production from stably incorporated constructs of the invention from regenerated transformed, preferably co-transformed protonema can be achieved. All references discussed herein, inasmuch as they may be required to supplement the present disclosure, are incorporated herein in their entirety by reference.

The invention will now be further described with reference to the following non-limiting Figures and Examples. Other embodiments of the invention will occur to those skilled in the art in the light of these.

EXAMPLES

Methods and Materials
Plant Material

The wild-type strain of *Physcomitrella patens* (Hedw.) B. S. G. (Reski et al. 1994) is used. It is a subculture of strain 16/14 which was collected by H. L. K. Whitehouse in Gransden Wood, Huntingdonshire, UK and propagated by Engel (1968).

Construction of Vectors
Construction of pRT101VEGF C3

Human vascular endothelial growth factor 121 ($VEGF_{121}$) cDNA without leader sequence is excised as an NdeI-SalI fragment from $pCYTEXP-VEGF_{121}$ (GBF, Braunschweig, Germany). This fragment is blunted by the Klenow reaction and introduced into pRT101 (Töpfer et al. 1987) at the SmaI restriction site to form plasmid pRT101VEGF C3. In this construct, the $VEGF_{121}$ cDNA minus leader sequence was placed downstream of the CaMV 35 S promoter and behind the CaMV terminator (Gorr, 1999).

Construction of pRT101TPVEGF C3

The sequence for VEGF signal peptide (sorting signal for secretion) is cloned into pRT101VEGF C3. The signal peptide cDNA is amplified from the plasmid pRT101 P21(Gorr, 1999) using the 5' primer MoB323 (5'-ATA CTC GAG GAA GAT GAA CTT TTC TGC CTG TCT TGG-3', SEQ ID NO 1) containing an XhoI restriction side and 3' primer MoB349 (5'-CTG CCA TGG GTG CAG CCT GGG ACC AC-3', SEQ ID NO 2) containing NcoI restriction side. The amplified DNA is digested with XhoI and NcoI and ligated into pRT101VEGF C3 (XhoI/NcoI digested) resulting in pRT101TPVEGF C3. The resulting plasmid contains the coding sequences for the VEGF signal peptide and $VEGF_{121}$ in frame under control of the CaMV 35 S promoter.

Cloning Procedure for 5' First Recombination Sequence into pRT99

The 250 bp 5' sequence of the $5^{th}$ intron: (5'-GCGGAAAT-GTTCAGAGTTAAGCGAAATCACAAC-TAAAAGAGATTGGAAGCAGAAGAATT TTTGAG-CAGCTGTTCTTAATTCACGCAACGACAACGCTATTA-ACTGTATGTGTAGACGAT GCACTTTCGTACT-GAAGGGATCTAAATTTATTATATCCCT-TCATAACTAGAGGCAAGGCG GAAATCACAAAAC-TATTGGTACCTACGTACTACAGCCTCCAGGATCAAA-CATAAGAGTGA AACACTGGACC-3', SEQ ID NO 3) of the alpha 1,3-fucosyltransferase gene of *Physcomitrella patens* is amplified from genomic DNA of *Physcomitrella patens* by Pfu-proof-reading PCR (Promega, Germany) using the upstream primer Rec1_SalI_SacII (5'-GAG GTC GAC CCG CGG AAA TGT TCA GAG-3', SEQ ID NO 4) and the downstream primer Rec1_SmaI (5'-CTC CCC GGG TCC AGT GTT TCA CTC-3', SEQ ID NO 5). After restriction of the resulting amplification product with SalI and SmaI it is cloned into the vector pRT99 (Töpfer et al. 1988) (SalI and SmaI digested). The resulting plasmid pRT99Rec1 contains the 5' first recombination sequence.

Cloning Procedure for the 3' Second Recombination Sequence into pRT99Rec1

The 208 bp 3' sequence of the $5^{th}$ intron: (5'-GGGAC-CCAAGCGTAAGAAGTCTTATGAAAAAGT-TACCTCACAGATTAAAACTAAACATAGGA AAATAC-CAATGCACTCCAATGTGTCAATGAGATTAACGCTT-GACTAACATGAAAATATAA ATATTCACCGAAT-GAAAGAAATTAGAAAACAGGACCTGTA-GATTGTAAGAGATAGATTCT TGAGTTAGAAACA-CAAATGATTGTCC-3', SEQ ID NO 6) of the alpha 1,3-fucosyltransferase gene of *Physcomitrella patens* is amplified from genomic DNA of *Physcomitrella patens* by Pfu-proof-reading PCR (Promega, Germany) using the upstream primer Rec11_SmaI (5'-GAG CCC GGG ACC CAA GCG TAA GAA G-3', SEQ ID NO 7) and the downstream primer Rec11_SacII_SstII (5'-TCT GAG CTC CCG CGG ACA ATC ATT TGT GTT TC-3', SEQ ID NO 8). After restriction of the resulting amplification product with SmaI and SstI it is cloned into the vector pRT99Rec1 (SmaI and SstI digested). The resulting plasmid pRT99Rec11 contains the 5' first and the 3' second recombination sequence.

Construction of pRT99TPVEGFRec1

The expression cassette containing the CaMV 35S promoter, TPVEGF121 and CaMV 35S terminator is excised as a PstI fragment from pRT101TPVEGF C3. This fragment is blunted by the Klenow reaction and introduced into the SmaI digested and dephosphorylated plasmid pRT99Rec11 resulting in the plasmid pRT99TPVEGFRec1.

Cloning Procedure for 5' Second Recombination Sequence into pRT99

The 208 bp 3' sequence of the $5^{th}$ intron: (5'-GGGAC-CCAAGCGTAAGAAGTCTTATGAAAAAGT-TACCTCACAGATTAAAACTAAACATAGGA AAATAC-CAATGCACTCCAATGTGTCAATGAGATTAACGCTT-GACTAACATGAAAATATAA ATATTCACCGAAT-GAAAGAAATTAGAAAACAGGACCTGTA-GATTGTAAGAGATAGATTCT TGAGTTAGAAACA-CAAATGATTGTCC-3', SEQ ID NO 6) of the alpha 1,3-fucosyltransferase gene of *Physcomitrella patens* is amplified from genomic DNA of *Physcomitrella patens* by Pfu-proof-reading PCR (Promega, Germany) using the upstream primer Rec2_SalI_SacII (5'-GAG GTC GAC CCG CGG ACC CAA GCG TAA GAA G-3', SEQ ID NO 9) and the downstream primer Rec2_SmaI (5'-TCT CCC GGG ACA ATC ATT TGT GTT TC-3', SEQ ID NO 10). After restriction of the resulting amplification product with SalI and SmaI it is cloned into the vector pRT99 (Töpfer et al. 1988) (SalI and SmaI digested). The resulting plasmid pRT99Rec2 contains the 5' second recombination sequence.

Cloning Procedure for 3' First Recombination Sequence into pRT99Rec2

The 250 bp 51 sequence of the $5^{th}$ intron: (5'-GCGGAAAT-GTTCAGAGTTAAGCGAAATCACAAC-TAAAAGAGATTGGAAGCAGAAGAATT TTTGA-GCAGCTGTTCTTAATTCACGCAACGA-CAACGCTATTAACTGTATGTGTAGACGAT GCACTTTCGTACTGAAGGGATCTAAATT-TATTATATCCCTTCATAACTAGAGGCAAGGCG GAAATCACAAAACTATTGGTACCTACG-TACTACAGCCTCCAGGATCAAACATAAGAGTGA AACACTGGACC-3', SEQ ID NO 3) of the alpha 1,3-fucosyltransferase gene of *Physcomitrella patens* is amplified from genomic DNA of *Physcomitrella patens* by Pfu-proof-reading PCR (Promega, Germany) using the upstream primer Rec22_SmaI (5'-GAG CCC GGG AAA TGT TCA GAG TTA AGC G-3', SEQ ID NO 11) and the downstream primer Rec22_SacII_SstI (5'-TCT GAG CTC CCG CGG TCC AGT GTT TCA CTC TTA TG-3', SEQ ID NO 12). After restriction of the resulting amplification product with SmaI and SstI it is cloned into the vector pRT99Rec2 (SmaI and SstI digested). The resulting plasmid pRT99Rec22 contains the 5' second and the 3' first recombination sequences.

Construction of pRT99TPVEGFRec2

The expression cassette containing CaMV 35S promoter, $TPVEGF_{121}$ and CaMV 35S terminator is excised as a PstI fragment from pRT101TPVEGF C3. This fragment is blunted by the Klenow reaction and introduced into the SmaI digested and dephosphorylated plasmid pRT99Rec22 resulting in the plasmid pRT99TPVEGFRec2. Restriction of pRT99TPVEGFRec1 and Rec2 with SacII or SalI and SstI results in linearisation of the first and the second heterologous nucleic acid sequences comprising the recombination sequences and the heterologous nucleic acid sequences of interest comprising a promoter operably linked thereto. The linearised heterologous nucleic acid sequences are used for transformation of moss cells.

Standard Culture Conditions

Plants are grown axenically under sterile conditions in plain inorganic liquid modified Knop medium (1000 mg/l $Ca(NO_3)_2 \times 4H_2O$ 250 mg/l KCl, 250 mg/l $KH_2PO_4$, 250 mg/l $MgSO_4 \times 7H_2O$ and 12.5 mg/l $FeSO_4 \times 7H_2O$; pH 5.8 (Reski and Abel 1985)). Plants are grown in 500 ml Erlenmeyer flasks containing 200 ml of culture medium and the flasks are shaken on a Certomat R shaker (B. Braun Biotech International, Germany) set at 120 rpm. Conditions in the growth chamber are 25+/−3° C. and a light:dark regime of 16:8 h. The flasks are illuminated from above by two fluorescent tubes (Osram L 58 W/25) providing 35 $\mu mols^{-1}m^{-2}$. The cultures are sub-cultured once a week via disintegration using an Ultra-Turrax homogenizer (IKA, Staufen, Germany) and inoculation of two new 500 ml Erlenmeyer flasks containing 100 ml fresh Knop medium.

Protoplast Isolation

Pre-culture of moss tissue for optimal protoplast isolation. Mosses (especially *Physcomitrella patens*) can be pre-cultured under different conditions to obtain optimal protoplast yields:

I. Rother et al. 1994 cultivated moss tissue for 7 days in Knop medium with reduced (10%) $Ca(NO_3)_2$ content. Cultures are filtered 3 or 4 days after disintegration and are transferred into fresh Knop medium with reduced (10%) $Ca(NO_3)_2$ content.

II. Instead of reduction of $Ca(NO_3)_2$ the medium for pre-culture can be supplemented with 5 mM ammonium tartrate or the pH can be altered to 4.5 (in liquid cultures with uncontrolled pH-values an average pH of 5.8 is reached for modified Knop medium). Cultures are filtered 3 or 4 days after disaggregation of tissue and are transferred into fresh modified Knop medium (supplemented with 5 mM ammonium tartrate or altered to pH 4.5).

III. Hohe and Reski (2002) optimised culture conditions in a semi-continuous bioreactor to obtain high yields of protoplasts. Isolated protoplasts of high yields are obtained either by supplementation of modified Knop medium (Reski and Abel 1985) with 460 mg/l ammonium tartrate or under controlled pH-values with a setpoint of 4.5 (in bioreactor cultures with uncontrolled pH-values an average pH of 5.8 is reached for modified Knop medium).

Different protocols for the isolation of protoplasts (Grimsley et al. 1977; Schaefer et al. 1991; Rother et al. 1994; Zeidler et al. 1999; Hohe and Reski 2002, Protocol Schaefer 2001) and for transformation (Schaefer et al. 1991; Reutter and Reski 1996, Protocol Schaefer 2001) have been described for *Physcomitrella patens*.

For the work presented herein, a modification/combination of the previously described methods is used:

After filtration the moss protonemata are preincubated in 0.5 M mannitol. After 30 min, 4% Driselase (Sigma, Deisenhofen, Germany) is added to the suspension. Driselase is dissolved in 0.5 M mannitol (pH 5.6-5.8), centrifuged at 3600 rpm for 10 min and sterilised by passage through a 0.22 µm filter (Millex GP, Millipore Corporation, USA). The suspension, containing 1% Driselase (final concentration), is incubated in the dark at RT and agitated gently (best yields of protoplasts are achieved after 2 hours of incubation) (Protocol Schaefer 2001). The suspension is passed through sieves (Wilson, CLF, Germany) with pore sizes of 100 µm and 50 µm. The suspension is centrifuged in sterile centrifuge tubes and protoplasts are sedimented at RT for 10 min at 55 g (acceleration of 3; slow down at 3; Multifuge 3 S—R, Kendro, Germany) (Protocol Schaefer 2001). Protoplasts are gently re-suspended in W5 medium (125 mM $CaCl_2 \times 2H_2O$; 137 mM NaCl; 5.5 mM glucose; 10 mM KCl; pH 5.6; 660-680 mOsm; sterile filtered). The suspension is centrifuged again at RT for 10 min at 55 g (acceleration of 3; slow down at 3; Multifuge 3 S-R, Kendro, Germany). Protoplasts are gently re-suspended in W5 medium (Rother et al. 1994). For counting protoplasts a small volume of the suspension is transferred to a Fuchs-Rosenthal-chamber.

Transformation Protocol

For transformation protoplasts are incubated on ice in the dark for 30 minutes. Subsequently, protoplasts are sedimented by centrifugation at RT for 10 min at 55 g (acceleration of 3; slow down at 3; Multifuge 3 S-R, Kendro). Protoplasts are re-suspended in 3M medium (15 mM $CaCl_2 \times 2H_2O$; 0.1% MES; 0.48 M mannitol; pH 5.6; 540 mOsm; sterile filtered, Schaefer et al. 1991) at a concentration of $1.2 \times 10^6$ protoplasts/ml (Reutter and Reski 1996). 250 µl of this protoplast suspension are dispensed into a new sterile centrifuge tube, 50 µl DNA solution of both constructs, pRT99TPVEGFRec1 and pRT99VEGFRec2, and the vector containing the selection marker (column purified DNA in $H_2O$ (Qiagen, Hilden, Germany); 10-100 µl; DNA amount of 30 µg per construct; 10 µg of the vector containing the selection marker) is added and finally 250 µl PEG-solution (40% PEG 4000; 0.4 M mannitol; 0.1 M $Ca(NO_3)_2$; pH 6 after autoclaving) is added. The suspension is immediately but gently mixed and then incubated for 6 min at RT with occasional gentle mixing. The suspension is diluted progressively by adding 1, 2, 3 and 4 ml of 3M medium. The suspension is centrifuged at 20° C. for 10 minutes at 55 g (acceleration of 3; slow down at 3; Multifuge 3 S-R, Kendro). The pellet is re-suspended in 3 ml regeneration medium. Selection procedure is performed as described by Strepp et al. (1998).

DNA Analysis

DNA analysis of stably transformed plants is performed as described by Strepp et al. (1998). Estimation of copy number is performed by Southern blot analysis and comparison to a stably transformed plant containing one copy of the heterologous DNA.

Assays

Quantification of Recombinant $VEGF_{121}$

Recombinant $VEGF_{121}$ expressed by stably transformed moss plants is quantified by ELISA (R&D Systems, Wiesbaden, Germany). The ELISA is performed according to the instructions of the manufacturer. The samples can be diluted for quantification.

Results

For stably transformed plants the estimation of high copy numbers of integrated constructs correlates with high yields of recombinant protein.

LITERATURE

Engel P P (1968) The induction of biochemical and morphological mutants in the moss *Physcomitrella patens*. Am J Bot 55, 438-446.

Gorr G (1999) Biotechnologische Nutzung von *Physcomitrella patens* (Hedw.) B. S. G. Dissertation, Universität Hamburg.

Grimsley N H, Ashton N W and Cove D J (1977) The production of somatic hybrids by protoplast fusion in the moss, *Physcomitrella patens*. Mol Gen Genet. 154, 97-100.

Hohe A, Reski R (2002) Optimisation of a bioreactor culture of the moss *Physcomitrella patens* for mass production of protoplasts. Plant Sci 163, 69-74.

Reski R, Abel W O (1985) Induction of budding on chloronemata and caulonemata of the moss, *Physcomitrella patens*, using isopentenyladenine. *Planta* 165, 354-358.

Reski R, Faust M, Wang X-H, Wehe M, Abel W O (1994) Genome analysis of the moss *Physcomitrella patens* (Hedw.) B. S. G. *Mol Gen Genet*. 244, 352-359.

Rother S, Hadeler B, Orsini J M, Abel W O and Reski R (1994) Fate of a mutant macrochloroplast in somatic hybrids. *J Plant Physiol* 143, 72-77.

Reutter K and Reski R (1996) Production of a heterologous protein in bioreactor cultures of fully differentiated moss plants. *Plant Tissue Culture and Biotechnology* 2, 142-147.

Schaefer D, Zryd J-P, Knight C D and Cove D J (1991) Stable transformation of the moss *Physcomitrella patens*. *Mol Gen Genet*. 226, 418-424.

Schaefer D G (2001) Principles and protocols for the moss *Physcomitrella patens*. http://www.unil.ch/lpc/docs/PPprotocols2001.pdf Strepp R, Scholz, S, Kruse, S, Speth V and Reski, R (1998) Plant nuclear gene knockout reveals a role in plastid division for the homologue of the bacterial cell division protein FtsZ, an ancestral tubulin. *Proc Natl Acad Sci USA* 95, 4368-4373.

Töpfer R, Matzeit V, Gronenborn B, Schell J and Steinbiss H-H (1987) A set of plant expression vectors for transcriptional and translational fusions. *NAR* 15, 5890.

Töpfer, R, Schell, J and Steinbiss, H-H (1988) Versatile cloning vectors for transient gene expression and direct gene transfer in plant cells. *NAR* 16, 8725.

The invention claimed is:

1. A method of amplifying gene expression in a moss plant cell by increasing the copy number of integrated transforming DNA constructs, the method comprising:
   1) providing at least a first heterologous nucleic acid construct comprising at least one heterologous nucleotide sequence operably linked to a promoter, wherein said construct is flanked at the 5' end thereof by a first recombination sequence and is flanked at the 3' end of said construct by a second recombination sequence;
   2) providing at least a second heterologous nucleic acid construct different from the first, said second construct comprising at least one heterologous nucleotide sequence operably linked to a promoter, wherein said construct is flanked at the 5' end thereof by said second recombination sequence and is flanked at the 3' end of said construct by said first recombination sequence;
   3) transforming into the moss plant cell at least said first and said second heterologous nucleic acid constructs; and
   4) regenerating the transformed moss plant cell into moss protonema comprising a plurality of copies of said at least one heterologous nucleotide sequence;
      wherein said first recombination sequence differs from said second recombination sequence and wherein recombination occurs between said different constructs at said first recombination sequences and at said second recombination sequences after transformation.

2. A method according to claim 1 wherein said at least first construct and said at least second construct are co-transformed into a moss protoplast.

3. A method according to claim 1 wherein the recombination sequences are selected from the group consisting of genomic DNA and cDNA.

4. A method according to claim 3 wherein the recombination sequence is selected from an intron or non-coding region.

5. A method according to claim 3 wherein the length of the recombination sequences is from 25 to 1000 nucleotides long.

6. A method according to claim 5 wherein the length of the recombination sequences is from 50-650 nucleotides long.

7. A method according to claim 6 wherein the length of the recombination sequences is from 100-400 nucleotides long.

8. A set of nucleic acid vectors suitable for amplifying gene expression in a moss plant cell, wherein said set of nucleic acid vectors comprises:
   1) at least a first heterologous nucleic acid construct comprising at least one heterologous nucleotide sequence operably linked to a promoter, wherein said construct is flanked at the 5' end thereof by a first recombination sequence and is flanked at the 3' end of said construct by a second recombination sequence; and
   2) at least a second heterologous nucleic acid construct different from the first, said second construct comprising at least one heterologous nucleotide sequence operably linked to a promoter, wherein said construct is flanked at the 5' end thereof by said second recombination sequence and is flanked at the 3' end of said construct by said first recombination sequence;
      wherein said first recombination sequence differs from said second recombination sequence,
      wherein said first and said second recombination sequences permit recombination in vivo between said different constructs at said first recombination sequences and at said second recombination sequences, and
      wherein said first and second recombination sequences are homologous to sequences in the moss plant cell's genome thereby permitting integration of heterologous sequences obtained from said recombination into the moss plant cell's genome.

9. A set of nucleic acid vectors according to claim 8, wherein the constructs are linear DNA constructs.

10. A moss cell transformed with a set of nucleic acid vectors suitable for amplifying gene expression in a moss plant cell, wherein said set of nucleic acid vectors comprises:
1) at least a first heterologous nucleic acid construct comprising at least one heterologous nucleotide sequence operably linked to a promoter, wherein said construct is flanked at the 5' end thereof by a first recombination sequence and is flanked at the 3° end of said construct by a second recombination sequence; and
2) at least a second heterologous nucleic acid construct different from the first, said second construct comprising at least one heterologous nucleotide sequence operably linked to a promoter, wherein said construct is flanked at the 5' end thereof by said second recombination sequence and is flanked at the 3' end of said construct by said first recombination sequence;
wherein said first recombination sequence differs from said second recombination sequence and wherein said first and said second recombination sequences permit recombination in vivo between said different constructs at said first recombination sequences and at said second recombination sequences.

11. A moss cell according to claim 10 which is a moss protoplast or a moss protonema cell.

12. A moss cell according to claim 11 which is *Physcomitrella patens*.

13. Moss protonema tissue comprised of cells transformed with a set of nucleic acid vectors suitable for amplifying gene expression in a moss plant cell, wherein said set of nucleic acid vectors comprises:
1) at least a first heterologous nucleic acid construct comprising at least one heterologous nucleotide sequence operably linked to a promoter, wherein said construct is flanked at the 5' end thereof by a first recombination sequence and is flanked at the 3' end of said construct by a second recombination sequence; and
2) at least a second heterologous nucleic acid construct different from the first, said second construct comprising at least one heterologous nucleotide sequence operably linked to a promoter, wherein said construct is flanked at the 5° end thereof by said second recombination sequence and is flanked at the 3° end of said construct by said first recombination sequence;
wherein said first recombination sequence differs from said second recombination sequence and wherein said first and said second recombination sequences permit recombination in vivo between said different constructs at said first recombination sequences and at said second recombination sequences.

14. Use of moss protonema cells transformed with a set of nucleic acid vectors in the production of protein therefrom, comprising
1) providing moss protonema cells transformed with the set of DNA vectors suitable for amplifying gene expression in a moss plant cell, wherein said set of nucleic acid vectors comprises:
   a) at least a first heterologous nucleic acid construct comprising at least one heterologous nucleotide sequence operably linked to a promoter, wherein said construct is flanked at the 5' end thereof by a first recombination sequence and is flanked at the 3' end of said construct by a second recombination sequence, and
   b) at least a second heterologous nucleic acid construct different from the first, said second construct comprising at least one heterologous nucleotide sequence operably linked to a promoter, wherein said construct is flanked at the 5' end thereof by said second recombination sequence and is flanked at the 3' end of said construct by said first recombination sequence;
   wherein said first recombination sequence differs from said second recombination sequence and wherein said first and said second recombination sequences permit recombination in vivo between said different constructs at said first recombination sequences and at said second recombination sequences; and
2) inducing expression of protein encoded in said DNA constructs.

15. Use according to claim 14 wherein said moss protonema cells are *Physcomitrella patens*.

16. A method according to claim 1 further wherein said recombination results in heterologous sequences, the method further comprising integrating said heterologous sequences into the moss plant cell's genome.

17. A set of nucleic acid vectors according to claim 8 wherein said recombination sequences are selected from the group consisting of a genomic DNA sequence and a cDNA sequence.

18. A method according to claim 1 wherein the recombination sequences are selected from the group consisting of an intron, a non-coding region, an exon, and a combination thereof.

19. A set of nucleic acid vectors according to claim 8 wherein said recombination sequences are selected from the group consisting of an intron sequence, a non-coding region sequence, an exon sequence, and a combination thereof.

* * * * *